(12) United States Patent
Litman et al.

(10) Patent No.: US 7,285,779 B2
(45) Date of Patent: Oct. 23, 2007

(54) METHODS OF SCANNING AN OBJECT THAT INCLUDES MULTIPLE REGIONS OF INTEREST USING AN ARRAY OF SCANNING BEAMS

(75) Inventors: Alon Litman, Nes Ziona (IL); Benzion Sender, Modiin (IL)

(73) Assignee: Applied Materials Israel, Ltd. (IL)

( * ) Notice: Subject to any disclaimer, the term of this patent is extended or adjusted under 35 U.S.C. 154(b) by 0 days.

(21) Appl. No.: 11/076,483

(22) Filed: Mar. 9, 2005

(65) Prior Publication Data
US 2005/0279936 A1    Dec. 22, 2005

Related U.S. Application Data

(60) Provisional application No. 60/581,817, filed on Jun. 21, 2004.

(51) Int. Cl.
*G01N 23/00* (2006.01)
*G21K 7/00* (2006.01)

(52) U.S. Cl. .............. 250/310; 250/310; 250/306; 250/307

(58) Field of Classification Search ............... 250/310, 250/306, 307
See application file for complete search history.

(56) References Cited

U.S. PATENT DOCUMENTS

| | | | |
|---|---|---|---|
| 6,038,018 A | 3/2000 | Yamazaki et al. | |
| 6,465,783 B1 * | 10/2002 | Nakasuji | 250/311 |
| 6,590,218 B1 | 7/2003 | Suzuki | |
| 6,738,506 B2 | 5/2004 | Miller et al. | |

FOREIGN PATENT DOCUMENTS

| | | |
|---|---|---|
| EP | 00377298 | 7/1994 |
| EP | 00289279 | 8/1994 |
| EP | 00518633 | 11/1997 |

* cited by examiner

*Primary Examiner*—Jack Berman
*Assistant Examiner*—Jennifer Yantorno
(74) *Attorney, Agent, or Firm*—Sonnenschein Nath & Rosenthal LLP

(57) ABSTRACT

A multi beam inspection method and system. The inspection system includes: (i) a beam array generator adapted to generate an array of beams characterized by a beam array axis; and (ii) at least one mechanism adapted to position the object under the array of beams such that at least two beams that are positioned along a beam array axis scan substantially simultaneously at least two regions of interest of the object, wherein the first axis is oriented in relation to the beam array axis.

18 Claims, 9 Drawing Sheets

 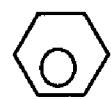 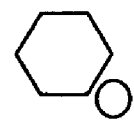
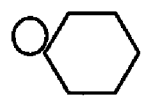  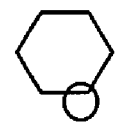
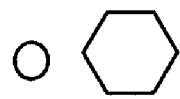 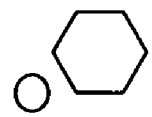 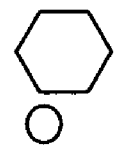
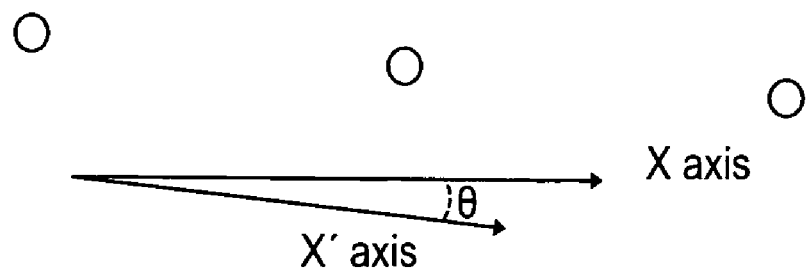
FIG. 5 determining a first spatial relationship between at least two regions of interest positioned along a region of interest axis
410 positioning, at least in response to the first spatial relationship, the object under multiple beams of an beam array, such that at least two beams of the beam array that are positioned along a beam array axis scan substantially simultaneously the at least two regions of interest, wherein the first axis is oriented in relation to the beam array axis
420 scanning the at least regions of interest
430

METHODS OF SCANNING AN OBJECT THAT INCLUDES MULTIPLE REGIONS OF INTEREST USING AN ARRAY OF SCANNING BEAMS

CROSS-REFERENCE TO RELATED APPLICATIONS

This application claims priority to U.S. Provisional Application titled "scanning regions of interest using a multi-beam system" filed Jun. 21, 2004, Ser. No. 60/581,817 which is incorporated herein by reference in its entirety.

FIELD OF THE INVENTION

The present invention relates to scanning an object that includes multiple regions of interest using an array of scanning beams, and especially of objects such as wafers or reticle using a charged particle beam array.

BACKGROUND OF THE INVENTION

Inspection of objects such as wafers or reticles using a scanning electron beam inspection tool is known in the art. Single beam inspection tools scan a wafer or reticle by a single beam. The relative size difference between wafers size and the beam cross section the throughput of such systems is limited.

In order to increase the throughput of inspection and metrology systems various techniques were suggested. A first technique include scanning only a portion of the wafer or reticle. This portion usually include multiple regions of interest that are positioned in various locations.

Another technique involves using multiple beam scanning arrays. Some multiple-beam systems include fixed arrays of beams, starting from line arrays to two dimensional grid arrays.

The following U.S. patents and U.S. patent applications, all being incorporated herein in reference, provide a brief overview of some state of the art multiple beam scanning systems: U.S. Pat. No. 6,465,783 of Nakasuji entitled "High-throughput specimen-inspection apparatus and methods utilizing multiple parallel charged particle beams and an array of multiple secondary-electron-detectors"; U.S. Pat. No. 6,734,428 of Parker et al. entitled "Multi-beam multi-column electron beam inspection system"; U.S. Pat. No. 6,750,455 of Lo et al. entitled "Methods and Apparatus for Multiple Charged Particle Beams"; U.S. Pat. No. 6,803,572 of Veneklasen, et al. entitled "Apparatus and methods for secondary electron emission microscope with dual beam"; and U.S. patent application publication No. 2002/0015143 of Yin et al. entitled "Multi-Beam Multi-Column Electron Beam Inspection System".

There is a need to provide an efficient system and method for scanning an object, using a multiple beam array.

SUMMARY OF THE INVENTION

The invention provides an inspection system that includes: (i) a beam array generator adapted to generate an array of beams characterized by a beam array axis; and (ii) at least one mechanism adapted to position the object under the array of beams such that at least two beams that are positioned along a beam array axis scan substantially simultaneously at least two regions of interest of the object, wherein the first axis is oriented in relation to the beam array axis.

Conveniently, the system further includes a controller adapted to determine a first spatial relationship between at least two regions of interest positioned along a region of interest axis. Conveniently, the at least one mechanism is adapted to rotate the object in relation to the array of beams. Conveniently, the at least one mechanism is adapted to rotate the array of beams in relation to object. Conveniently, the system is adapted to determine the spatial relationship by applying image processing.

Conveniently, the system is adapted to scan the at least two regions of interest, after the inspected object is positioned under the array of beams.

A method for inspecting an object that comprises multiple regions of interest, the method includes: determining a first spatial relationship between at least two regions of interest positioned along a region of interest axis; and positioning, at least in response to the first spatial relationship, the object under multiple beams of an beam array, such that at least two beams of the beam array that are positioned along a beam array axis scan substantially simultaneously the at least two regions of interest, wherein the first axis is oriented in relation to the beam array axis.

Conveniently, the stage of positioning comprises rotating the object in relation to the array of beams. Conveniently, the stage of positioning comprises rotating the array of beams in relation to the object. Conveniently, the stage of determining comprises image processing. Conveniently, the method further includes scanning the at least two regions of interest.

Conveniently, the aggregate area of the multiple regions of interest is relatively small in relation to the size of a surface of the object. Conveniently, the object is a wafer or a reticle. Conveniently, the array of beams includes a grid of beams.

Conveniently, the beams are charged particle beams. Conveniently, an orientation angle between the first axis and the beam array axis is responsive to a ratio of beam array spacing and between a region of interest spacing

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 4–6 illustrate exemplary relationships between beams and multiple regions of interest, according to various embodiments of the invention;

FIG. 8 is a flow chart of a method, according to an embodiment of the invention.

DETAILED DESCRIPTION OF THE INVENTION

In the following detailed description of the preferred embodiments and other embodiments of the invention, reference is made to the accompanying drawings. It is to be understood that those of skill in the art will readily see other embodiments and changes may be made without departing from the scope of the invention.

For convenience of explanation the following description relates to a system that inspects wafers by an array of electron beams. According to other embodiments of the invention the described system and method can be applied for metrology, for lithography and the like. The inspected object can be a reticle, a flat panel display, a MEMS device, and the like. The shape of the array can differ than a two dimensional grid, and the beams can include ion beams or light beams.

Figure 1:
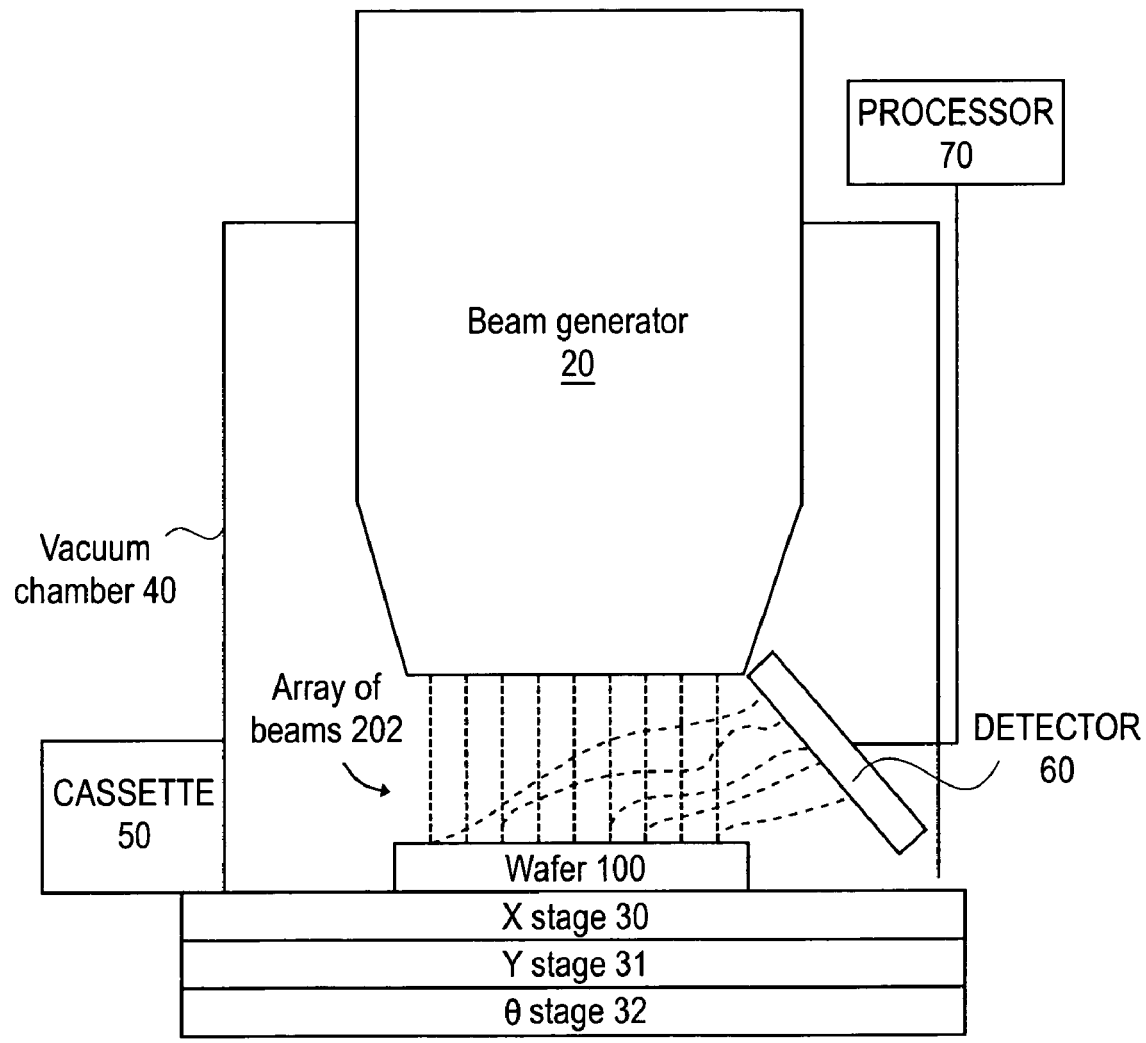
FIG. 1 illustrates an inspection system, according to an embodiment of the invention.

FIG. 1 illustrates an inspection system 10, according to an embodiment of the invention. System 10 includes a beam generator 20 that is capable of generating an array of charged particle beams 202. The beam generator 20 can be implemented in various manners. According to a first embodiment multiple tips generate multiple beams. According to another embodiment a single tip generates a beam that is later converted to multiple beams.

The beam generator 20 also includes optics that focus the array of beams onto an inspected object such as wafer 100. The wafer 100 is usually placed upon X, Y stages 30 and 31 and an optional Θ stage 32.

The wafer 100 is inspected within a vacuum chamber 40 and is inserted to the system 10 by a cassette 50 that has pre-alignment capabilities. These capabilities allows to insert the wafer at a certain tilt angle in relation to the imaginary X and Y axis of the stage. It is noted that a component other than the cassette 50 can have the pre-alignment capabilities. For example, a robot or a pre-aligner can perform the required rotation before the wafer is placed on the X-Y stages 30–31.

The system 10 further includes one or more detectors 60, and a processor 70 that is capable of receiving detector signals and locate defects. The processor 70 can also be used in an initial stage of locating the regions of interest. Said locating can include acquiring images of wafer portions until regions of interest are located.

The processor 70 can also be used to determine an orientation angle between the beam array and the inspected wafer. It is noted that processor 70 may include multiple components that are integrated with each other or can be located in various locations. For simplicity of explanation various components, including optics, were omitted.

It is noted that configuration illustrated in FIG. 1 is only one out of many possible configurations of an inspection system 10 can be of different architectures that the illustrated architecture.

Figure 2:
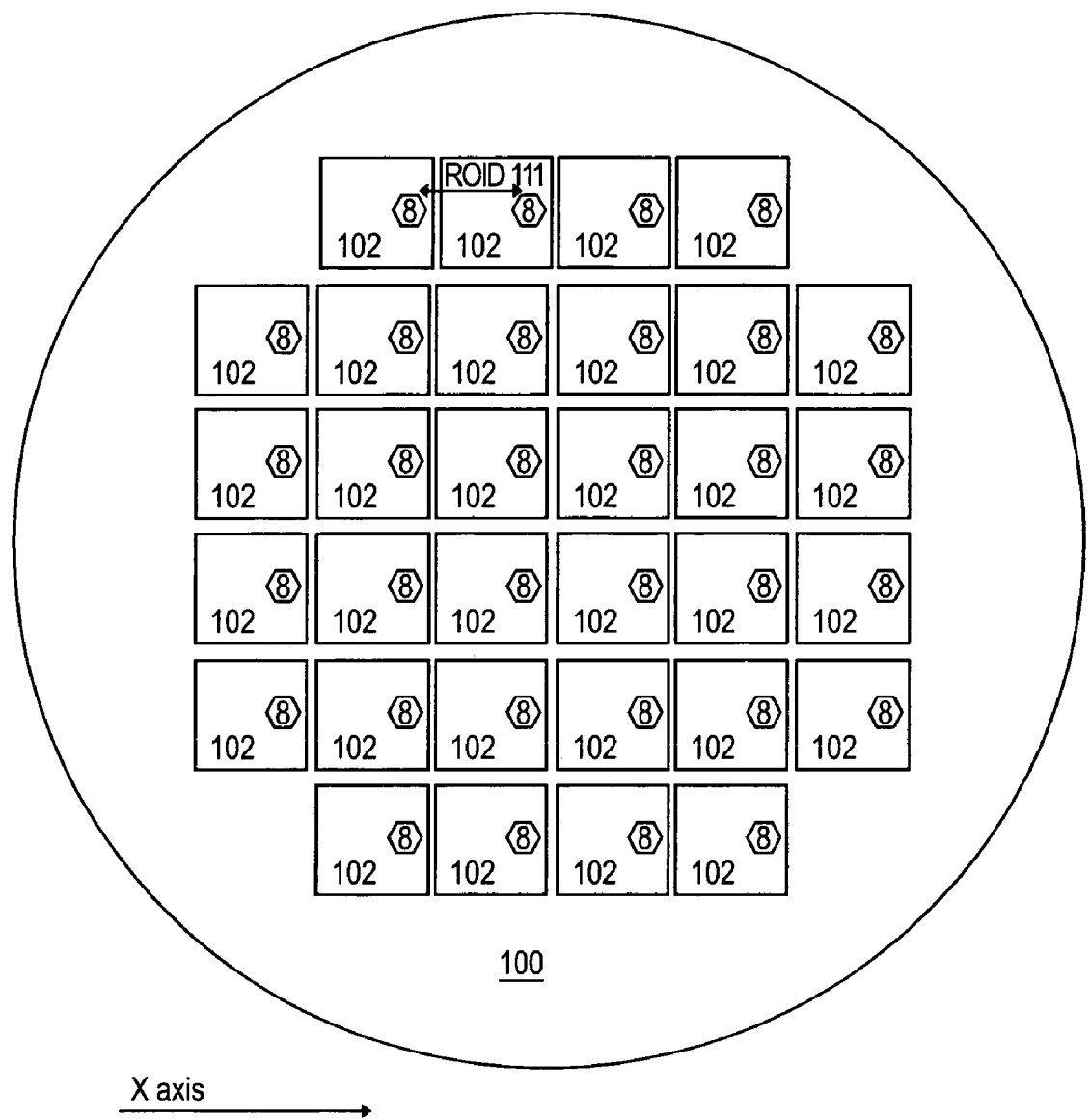
FIG. 2 illustrates a wafer that include multiple dies.

FIG. 2 illustrates wafer 100 that include multiple dies 102. In each die 102 there is at least one region of interest such as 8. It is assumed, for convenience of explanation, that each die includes a single region of interest and that all regions of interest are positioned in substantially the same position within the dies. It is further assumed that the regions of interest 8 are parallel to each other and are arranged in grid that corresponds to the arrangement of the multiple dies.

The distance between adjacent regions of interest, along a first axis such as an imaginary X axis, is defined as a region of interest spacing (ROID) 111. It is noted that other definitions may be used and that the imaginary axis X is used for simplifying the explanation only.

Dies are usually ideally identical to each other. Thus, the regions of interest are located at substantially the same position within each die. If a single region of interest is included within each die than the regions of interests that are included within the multiple dies conveniently have the same shape and are usually parallel to each other. This is not necessarily so, especially when the method is applied to inspect objects other than wafers. It is noted that when a die has more than a single region of interest than they can differ by shape, orientation, size and the like.

Figure 3:
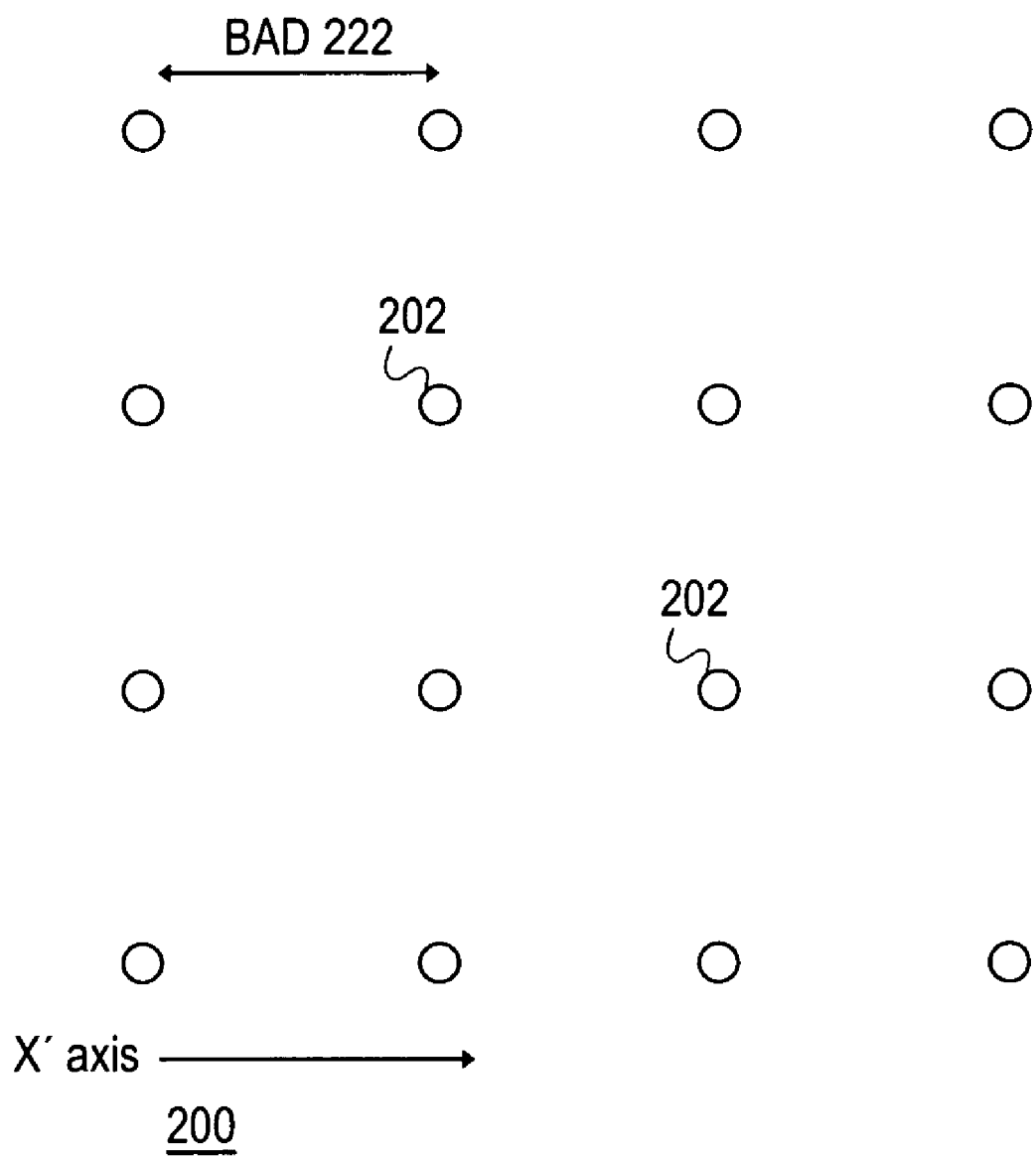
FIG. 3 illustrates multiple spots corresponding to multiple beams, according to an embodiment of the invention.

FIG. 3 illustrates multiple spots corresponding to multiple beams 202, according to an embodiment of the invention. The beams 202 of FIG. 2 form a regular grid. It is noted that although FIG. 1 and FIG. 2 illustrate an array of beam as well as an array of regions of interest that have the same shape (although may differ by the distance between adjacent members of the grid) this is not necessarily so.

The beams 202 of the beam array 200 form multiple columns along an imaginary beam array axis such as the X' axis. The distance between two adjacent beams along the X' axis is referred to beam array distance (BAD) 222.

If BAD 222 equals ROID 111 then wafer 100 can be positioned below a beam generator such that the first axis X is parallel to the first beam array axis X'. In such a case, multiple regions of interest can be placed beneath multiple beams of the array. The amount of simultaneously scanned regions of interest depends upon the amount of regions of interest and the amount of beams, assuming that the beam array has substantially the same shape as the imaginary grid formed by the regions of interest.

If BAD 222 differs than ROID 111 that there is a need to orient the beam array in relation to the wafer. The orientation can be achieved by various manners including rotating the wafer 100, rotating the beams 202 or rotating both. The rotation can be applied after the wafer 100 is placed into the inspection system or before it is provided below the beam array.

The rotation can also be achieved by various electrical, magnetic and/or electro-magnetic fields that rotate the beam array, or by a combination of such fields and mechanical means. Conveniently, the wafer in placed upon an X-Y and Θ stages 30-32.

The orientation angle is responsive to the relation between BAD 222 and ROID 111. In mathematical terms: $k*BAD=m*ROID*\cos(\theta)$, whereas $\theta$ is defined as the orientation angle between X axis and X' axis, m and k are positive integers.

It is noted that in some cases the equation can be satisfied by values of m and k that are not integer. If this is the case than the throughput of the system still can be greater than a single beam system. If k or m are almost integer than there can be a partial overlap between scanning a first region of interest by a first beam and scanning another region of interest, displaced by m ROIDs, by a beam displaced by almost K*BADs from the first beam.

Figure 4:
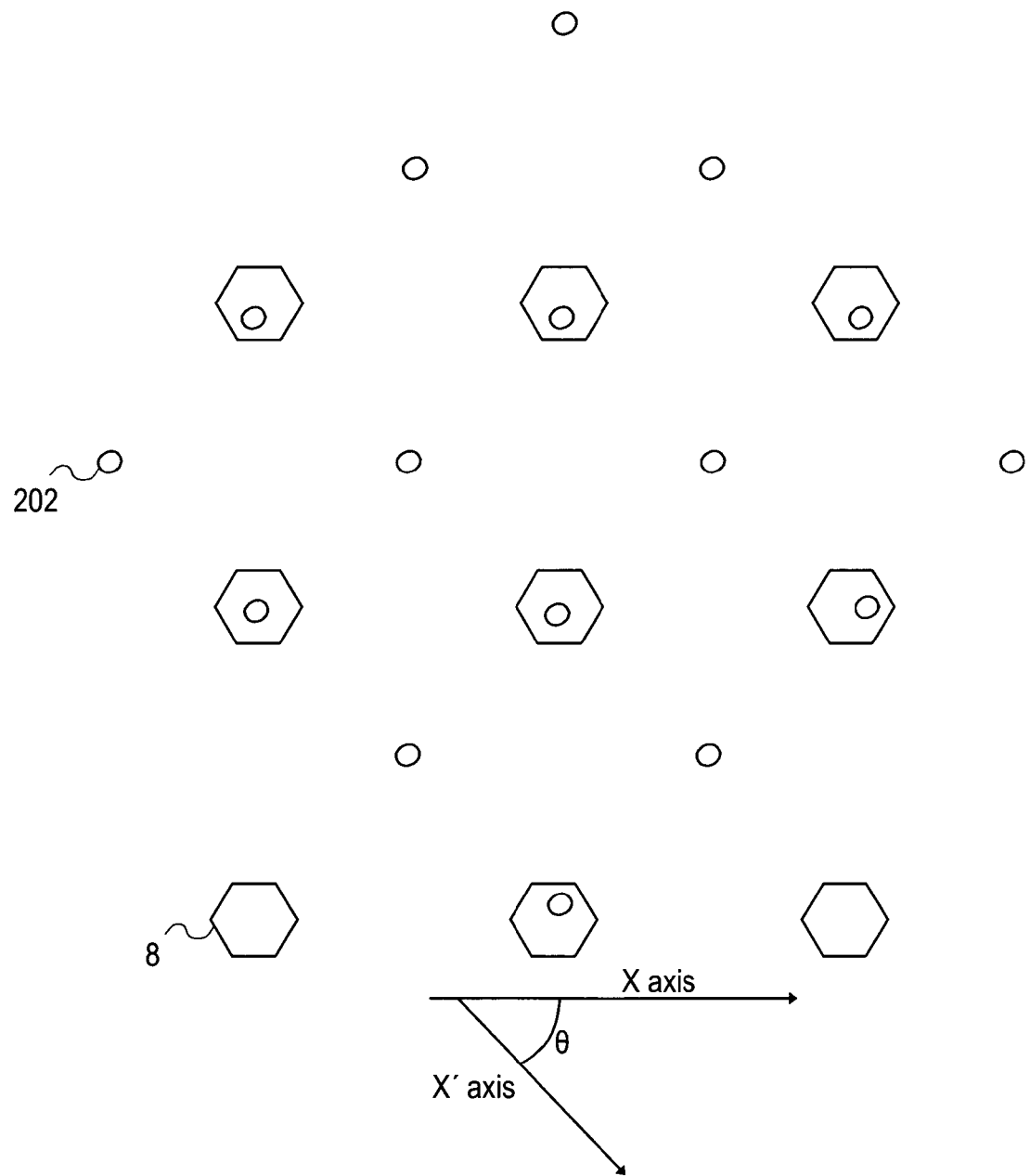
Figure 6:
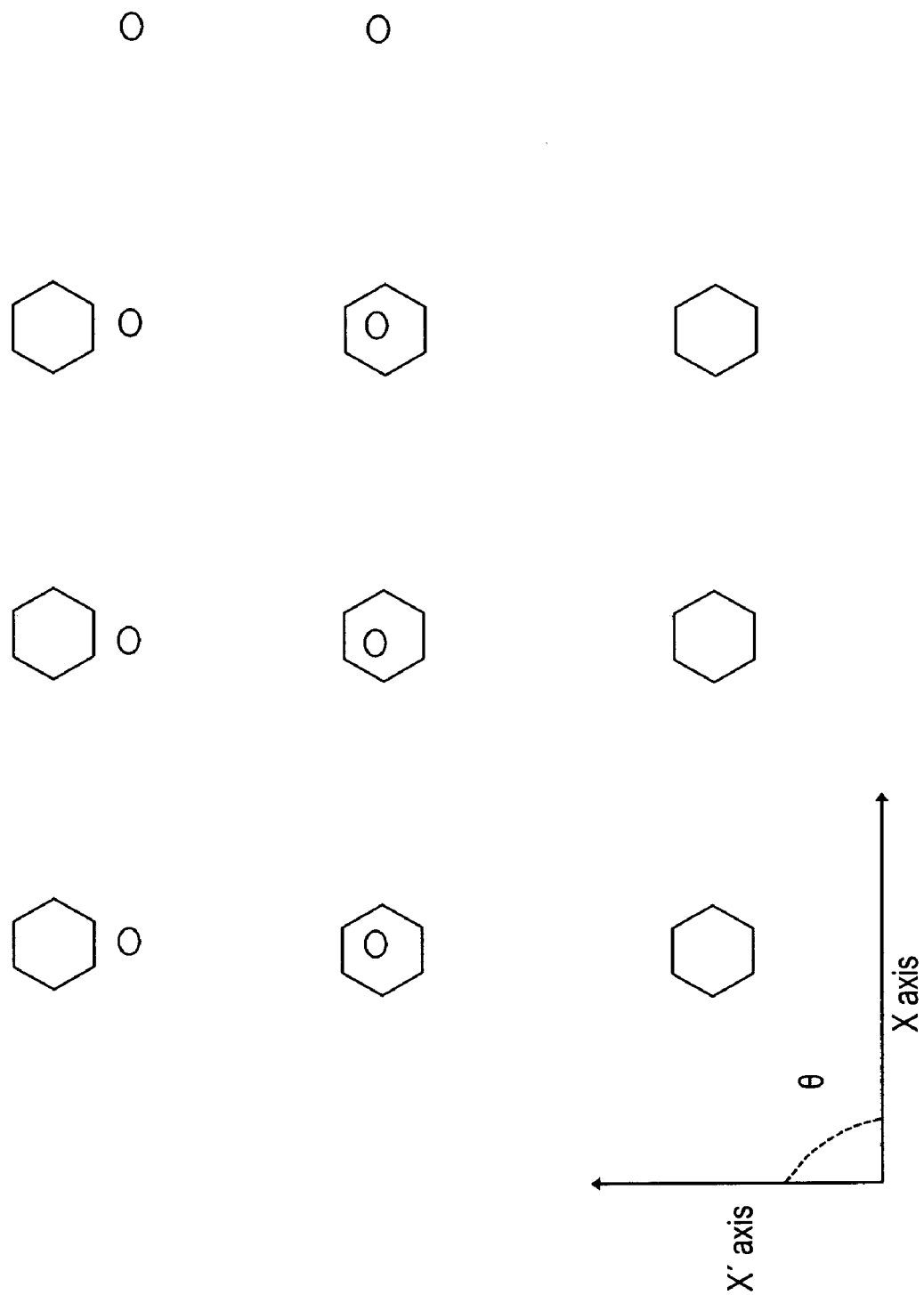

FIGS. 4–6 illustrate exemplary relationships between beams 202 and multiple regions of interest 8. FIGS. 4 and 5 illustrate an oblique orientation angle while FIG. 6 illustrates two rows of beams that were rotated by ninety degrees in order to scan multiple regions of interest. It is noted that these figures, as well as other figures of this specification are out of scale. Especially, the beams are usually much smaller than the regions of interest, although this is not necessarily so.

FIG. 4 illustrates a first exemplary relationship between beams 202 and regions of interest 8 in which.

According to an embodiment of the invention, additional areas, as well as the regions of interest can be scanned during the scanning process. These additional areas are usually defined in response to various parameters including scanning inaccuracies, region of interest location inaccuracies, difference in the respective locations of regions of interest within different dies, mechanical movement limitations, and the like.

As the wafer is usually moved along an imaginary axis, such as the Y axis, while the wafer is scanned. In many cases the continuous translation of the wafer causes the beams to scan areas that stretch between regions of interest.

Figure 7:
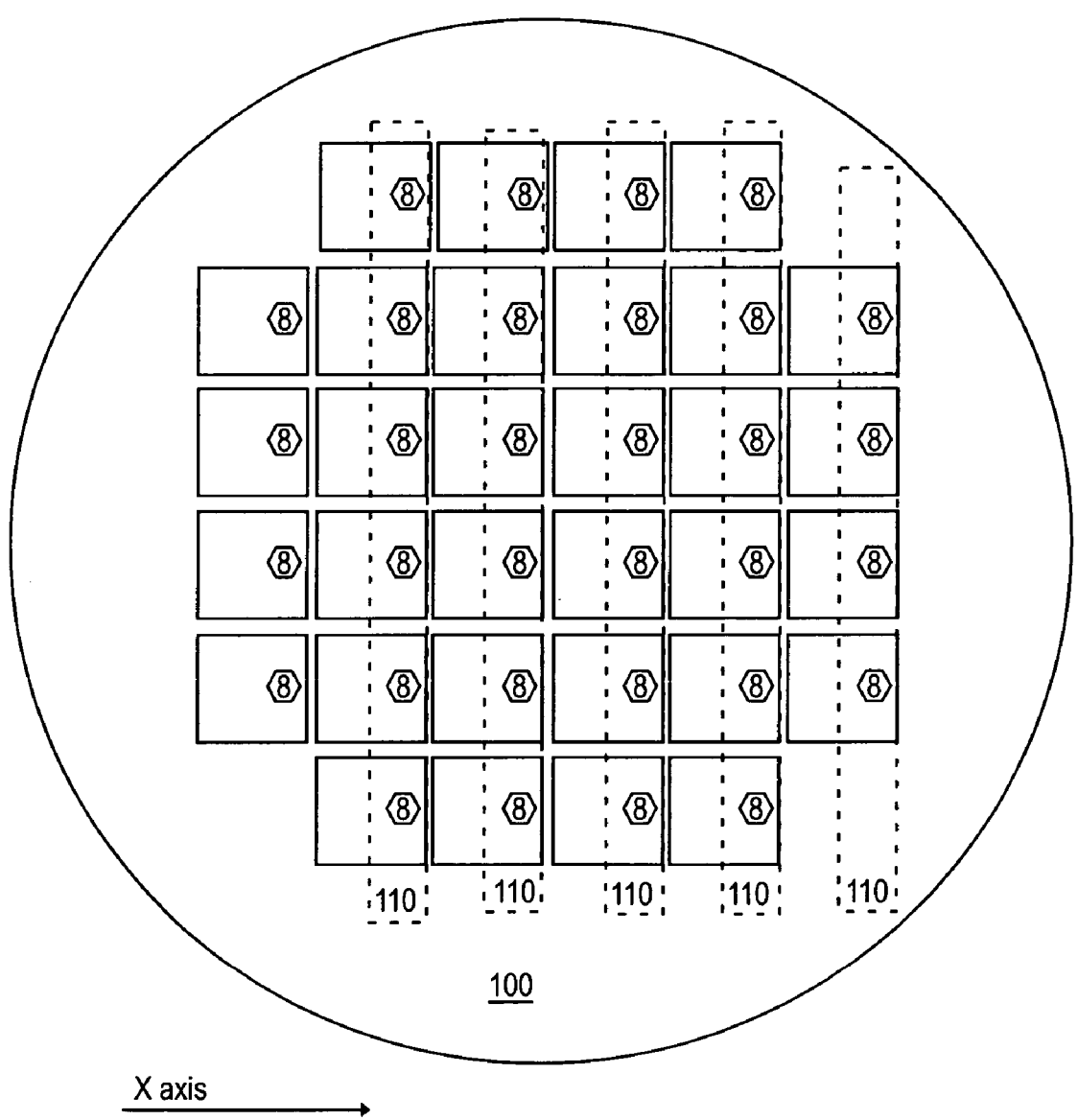
FIG. 7 illustrates multiple additional areas and regions of interest 8 that are scanned according to an embodiment of the invention.

FIG. 7 illustrates multiple additional areas 110 and regions of interest 8 that are scanned according to an embodiment of the invention. The additional areas 110 are slightly larger than the regions of interest 8. Each additional area 110 surrounds a column of regions of interest 8. It is noted that although FIG. 6 illustrates continuous additional areas than this is not necessarily so.

According to an embodiment of the invention the inspection system process signals only from regions of interests, but this is not necessarily so. The inspection system can apply various comparison methods including die to die, cell to cell and the like.

The inventors used an array of beams that included two rows of 5 beams each. It is noted that other arrays can be used, including arrays that include much more beams, as well as arrays that are shaped in different manners.

In one case, the regions of interest were arranges in columns and the inventors were able to increase throughput by applying an orientation angle of ninety degrees.

FIG. 8 is a flow chart of a method 400 for inspecting an object that includes multiple regions of interest.

Method 400 starts by stage 410 of determining a first spatial relationship between at least two regions of interest positioned along a region of interest axis. Conveniently, stage 410 includes rotating the object in relation to the array of beams. Conveniently, stage 410 includes rotating the array of beams in relation to the object. Conveniently, the beams are charged particle beams.

Stage 410 is followed by stage 420 of positioning, at least in response to the first spatial relationship, the object under multiple beams of an beam array, such that at least two beams of the beam array that are positioned along a beam array axis scan substantially simultaneously the at least two regions of interest, wherein the first axis is oriented in relation to the beam array axis.

Conveniently, an orientation angle between the first axis and the beam array axis is responsive to a ratio of beam array spacing and between a region of interest spacing. Conveniently, stage 420 involves image processing.

Stage 420 is followed by stage 430 of scanning the at least two regions of interest.

Conveniently, stage 420 includes orienting the object in relation to the beam array axis prior inserting the object into an inspection system that comprises array of beams generator.

Figure 9:
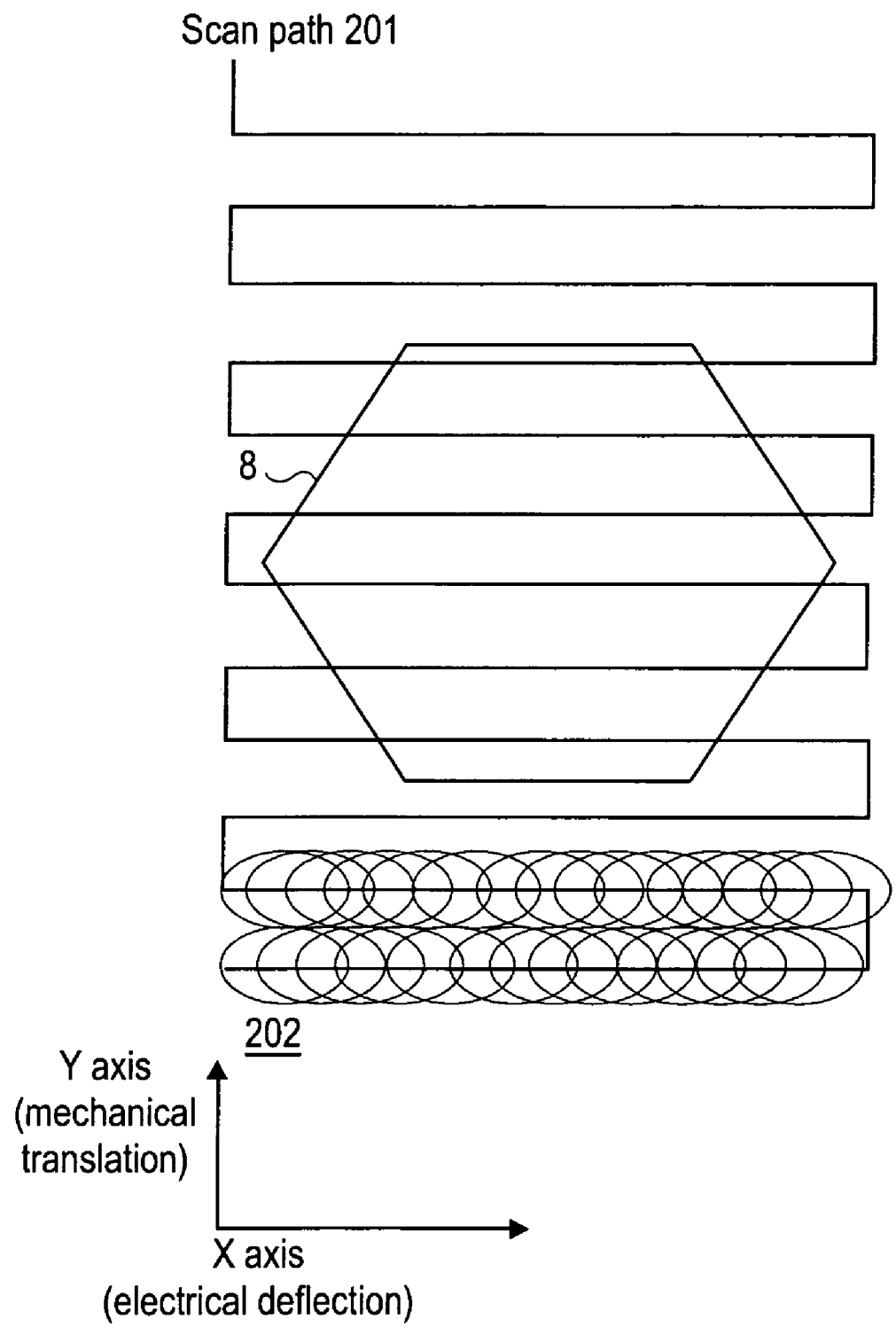
FIG. 9 illustrates a portion of a raster scan shaped scan path, according to an embodiment of the invention.

FIG. 9 illustrates a portion of a raster scan shaped scan path 201 that is by generated by mechanical movement along a Y axis and a deflection of a single beam along the X axis.

Conveniently, the aggregate area of the multiple regions of interest is relatively small in relation to the size of a surface of the object. Conveniently, the aggregate size of the scanned area Conveniently, the object is a wafer or a reticle. Conveniently, the array of beams includes a grid of beams.

The present invention can be practiced by employing conventional tools, methodology and components. Accordingly, the details of such tools, component and methodology are not set forth herein in detail. In the previous descriptions, numerous specific details are set forth, such as shapes of test structures and materials that are electro-optically active, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A method for inspecting an object that comprises multiple regions of interest, the method comprising:
   determining a first spatial relationship between at least two regions of interest positioned along a first axis; and
   positioning the object under multiple beams of a beam array having a beam array axis, such that at least two beams of the beam array irradiate substantially simultaneously the at least two regions of interest, wherein said positioning step comprises orienting the first axis in an angular relation to the beam array axis, the angular relation selected at least in response to the first spatial relationship wherein the beams are charged particle beams.

2. The method of claim 1 wherein the stage of positioning comprises rotating the object in relation to the array of beams.

3. The method of claim 1 wherein the stage of positioning comprises rotating the array of beams in relation to the object.

4. The method of claim 1 wherein an orientation angle between the first axis and the beam array axis is responsive to a ratio of beam array spacing and between a region of interest spacing.

5. The method of claim 1 wherein the stage of determining comprises image processing.

6. The method of claim 1 wherein the aggregate area of the multiple regions of interest is relatively small in relation to the size of a surface of the object.

7. The method of claim 1 wherein the object is a wafer or a reticle.

8. The method of claim 1 wherein the array of beams comprises a grid of beams.

9. The method of claim 1 wherein the stage of positioning comprises orienting the object in relation to the beam array axis prior to inserting the object into an inspection system that comprises an array of beams generator.

10. An inspection system, comprising:
    a beam array generator adapted to generate an array of beams having a beam array axis; and
    a processor adapted to determine a first spatial relationship between at least two regions of interest positioned along a first axis of an object; and
    at least one mechanism adapted to position the object under the array of beams and to orient the first axis in angular relation to the beam array axis such that at least two beams in the array of beams irradiate substantially simultaneously at least two regions of interest of the object wherein the beams are charged particle beams.

11. The system of claim 10 wherein the at least one mechanism is adapted to rotate the object in relation to the array of beams.

12. The system of claim 10 wherein the at least one mechanism is adapted to rotate the array of beams in relation to the object.

13. The system of claim 10 wherein an orientation angle between the first axis and the beam array axis is responsive to a ratio of beam array spacing and between a region of interest spacing.

14. The system of claim 10 adapted to determine by image processing the first spatial relationship between the at least two regions of interest positioned along the first axis.

15. The system of claim 10 wherein the aggregate area of the multiple regions of interest is relatively small in relation to the size of a surface of the object.

16. The system of claim 10 wherein the object is a wafer or a reticle.

17. The system of claim 10 wherein the array of beams comprises a grid of beams.

18. The system of claim 10 wherein the at least one mechanism is adapted to orient the object in relation to the beam array axis prior to inserting the object into the inspection system.

* * * * *